(12) United States Patent
Gadde et al.

(10) Patent No.: US 7,754,748 B2
(45) Date of Patent: *Jul. 13, 2010

(54) METHOD FOR TREATING OBESITY

(75) Inventors: Kishore M. Gadde, Durham, NC (US); K. Ranga R. Krishnan, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/205,769

(22) Filed: Sep. 5, 2008

(65) Prior Publication Data

US 2008/0319036 A1 Dec. 25, 2008

Related U.S. Application Data

(63) Continuation of application No. 10/830,071, filed on Apr. 23, 2004, now Pat. No. 7,425,571, which is a continuation of application No. 10/440,404, filed on May 19, 2003, now Pat. No. 7,109,198.

(60) Provisional application No. 60/380,874, filed on May 17, 2002.

(51) Int. Cl.
*A61K 31/42* (2006.01)

(52) U.S. Cl. .................................................. 514/379

(58) Field of Classification Search .................. 514/379
See application file for complete search history.

(56) References Cited

U.S. PATENT DOCUMENTS

| | | | |
|---|---|---|---|
| 3,819,706 A | 6/1974 | Mehta | |
| 3,885,046 A | 5/1975 | Mehta | |
| 4,089,855 A | 5/1978 | Chatterjie et al. | |
| 4,172,896 A | 10/1979 | Uno et al. | |
| 4,513,006 A | 4/1985 | Maryanoff et al. | |
| 4,673,679 A | 6/1987 | Aungst et al. | |
| 4,689,332 A | 8/1987 | McLaughlin et al. | |
| 4,855,306 A | 8/1989 | Markstein et al. | |
| 5,312,925 A | 5/1994 | Allen et al. | |
| 5,358,970 A | 10/1994 | Ruff et al. | |
| 5,403,595 A | 4/1995 | Kitchell et al. | |
| 5,426,112 A | 6/1995 | Zagon et al. | |
| 5,427,798 A | 6/1995 | Ludwig et al. | |
| 5,486,362 A | 1/1996 | Kitchell | |
| 5,512,593 A | 4/1996 | Dante | |
| 5,541,231 A | 7/1996 | Ruff et al. | |
| 5,719,197 A | 2/1998 | Kanios et al. | |
| 5,731,000 A | 3/1998 | Ruff et al. | |
| 5,763,493 A | 6/1998 | Ruff et al. | |
| 5,817,665 A | 10/1998 | Dante | |
| 5,856,332 A | 1/1999 | Dante | |
| 5,958,962 A | 9/1999 | Dante | |
| 6,004,970 A | 12/1999 | O'Malley et al. | |
| 6,034,091 A | 3/2000 | Dante | |
| 6,071,537 A | 6/2000 | Shank | |
| 6,071,918 A | 6/2000 | Cook | |
| 6,110,973 A | 8/2000 | Young | |
| 6,150,366 A | 11/2000 | Arenson et al. | |
| 6,191,117 B1 | 2/2001 | Kozachuk | |
| 6,197,827 B1 | 3/2001 | Cary | |
| 6,210,716 B1 | 4/2001 | Chen et al. | |
| 6,245,766 B1 | 6/2001 | Watsky | |
| 6,248,363 B1 | 6/2001 | Mahesh et al. | |
| 6,262,049 B1 | 7/2001 | Coffin et al. | |
| 6,274,579 B1 | 8/2001 | Morgan et al. | |
| 6,323,236 B2 | 11/2001 | McElroy | |
| 6,342,515 B1 * | 1/2002 | Masuda et al. | 514/379 |
| 6,344,474 B1 | 2/2002 | Maruani et al. | |
| 6,437,147 B1 | 8/2002 | Andersen et al. | |
| 6,441,038 B1 | 8/2002 | Cook | |
| 6,506,799 B1 | 1/2003 | Dasseux | |
| 6,541,478 B1 | 4/2003 | O'Malley et al. | |
| 6,548,551 B2 | 4/2003 | Hinz | |
| 6,569,449 B1 | 5/2003 | Stinchcomb et al. | |
| 6,686,337 B2 | 2/2004 | Connor | |
| 6,713,488 B2 | 3/2004 | Sadee et al. | |
| 6,905,708 B2 | 6/2005 | Li et al. | |
| 7,109,198 B2 * | 9/2006 | Gadde et al. | 514/238.8 |
| 7,425,571 B2 * | 9/2008 | Gadde et al. | 514/379 |
| 2001/0025038 A1 | 9/2001 | Coffin et al. | |
| 2002/0025972 A1 | 2/2002 | Hintz | |
| 2002/0037836 A1 | 3/2002 | Henriksen | |
| 2002/0090615 A1 | 6/2002 | Rosen et al. | |
| 2003/0055008 A1 | 3/2003 | Marcotte | |
| 2003/0144174 A1 | 7/2003 | Brenna et al. | |
| 2003/0144271 A1 | 7/2003 | Shulman | |
| 2004/0002462 A1 | 1/2004 | Najarian | |
| 2004/0029941 A1 | 2/2004 | Jennings | |
| 2004/0033965 A1 | 2/2004 | Gadde et al. | |
| 2004/0106576 A1 | 6/2004 | Jerussi et al. | |
| 2004/0122033 A1 | 6/2004 | Nargund et al. | |
| 2004/0198668 A1 | 10/2004 | Gadde et al. | |

(Continued)

FOREIGN PATENT DOCUMENTS

EP 0 442 769 A2 8/1991

(Continued)

OTHER PUBLICATIONS

"A Novel Twist on Binge Eating Treatment" Primary Psychiatry; 6(10) 24-29 (1999).

(Continued)

*Primary Examiner*—Raymond J Henley, III
(74) *Attorney, Agent, or Firm*—Knobbe, Martens, Olson & Bear, LLP

(57) ABSTRACT

The present invention relates, in general, to obesity, and, in particular, to a method of treating obesity and minimizing metabolic risk factors associated therewith using, for example, zonisamide or other weight-loss promoting anticonvulsant either alone or in combination with bupropion or other compound that enhances the activity of norepinephrine and/or dopamine via uptake inhibition or other mechanism.

12 Claims, 2 Drawing Sheets

U.S. PATENT DOCUMENTS

| | | |
|---|---|---|
| 2004/0242974 A1 | 12/2004 | Glover |
| 2004/0254208 A1 | 12/2004 | Weber et al. |
| 2005/0026986 A1 | 2/2005 | Maruani et al. |
| 2005/0137144 A1 | 6/2005 | Gadde et al. |
| 2005/0143322 A1 | 6/2005 | Gadde et al. |
| 2005/0154002 A1 | 7/2005 | Crooks et al. |
| 2005/0181070 A1 | 8/2005 | Gadde et al. |
| 2005/0215552 A1 | 9/2005 | Gadde et al. |
| 2005/0277579 A1 | 12/2005 | Krishnano et al. |
| 2006/0009514 A1 | 1/2006 | Gadde et al. |
| 2006/0058293 A1 | 3/2006 | Weber et al. |
| 2006/0079501 A1 | 4/2006 | Gadde et al. |
| 2006/0100205 A1 | 5/2006 | Weber et al. |
| 2006/0142290 A1 | 6/2006 | Weber et al. |
| 2006/0160750 A1 | 7/2006 | Gadde et al. |

FOREIGN PATENT DOCUMENTS

| | | |
|---|---|---|
| RU | 2214241 | 6/1996 |
| WO | WO 90/13294 | 11/1990 |
| WO | WO 96/09047 | 3/1996 |
| WO | WO 99/37305 | 7/1999 |
| WO | WO 00/50020 | 8/2000 |
| WO | WO 00/51546 | 9/2000 |
| WO | WO 00/76493 | 12/2000 |
| WO | WO 01/01973 A2 | 1/2001 |
| WO | WO 01/26641 A2 | 4/2001 |
| WO | WO 01/62257 | 8/2001 |
| WO | WO 02/09694 | 2/2002 |
| WO | WO 03/013524 | 2/2003 |
| WO | WO 03/092682 | 11/2003 |
| WO | WO 03/092682 A1 | 11/2003 |
| WO | WO 03/097046 | 11/2003 |
| WO | WO 2004/009015 | 1/2004 |
| WO | WO 2004/024096 | 3/2004 |
| WO | WO 2004/050020 | 6/2004 |
| WO | WO 2004/096201 | 11/2004 |
| WO | WO 2004/110368 | 12/2004 |
| WO | WO 2004/110375 | 12/2004 |
| WO | WO 2005/000217 | 1/2005 |
| WO | WO 2005/049043 | 6/2005 |
| WO | WO 2006/017504 | 2/2006 |

OTHER PUBLICATIONS

Anderson, et al. Bupropion SR enhances weight loss Obesity R., vol. 10, N. 7, 2002, pp. 633-641, XP002351373.

Altman and Bland. "Standard Deviations and Standard Errors," BMJ; 2005:331:903.

Appolinario et al. "Pharmacological Approaches in the Treatment of Binge Eating Disorder." Current Drug Targets; 5:301-307 (2004).

Aronne, et al. "Weight Gain in the Treatment of Mood Disorders"; J Clin Psychiatry 2003;64 (supple 8).

Asconape. "Some Common Issues in the Use of Antiepileptic Drugs." Seminars in Neurology; 22(1):27-39 (2002).

Atkinson, Clinical Guidelines on the identification, Evaluation, and pharamacologic treatment of obesity in Adults, Online, Jul. 25, 2003, URL:http://www.endotext.org.obesity/obesity15b/obesity15b.htm.

Ayala, "Weight Loss Associated With the Administration of Zonisamide", AES Proceedings, Epilepsia 41(Suppl. 7) :99 (2000)—No. 2.041.

Ayala et al, "Weight Loss Associated With the Administration of Zonisamide", A Compendium of Posters and Platform Sessions for ZONEGRAN™ and DIASTAT®, Presented at the Annual Meeting 2000 of the American Epilepsy Society, Dec. 1-6, 2000, Los Angeles, California.

Beelen, et al. "Asymptomatic QTC prolongation associated with queitiapine fumarate overdose in a patient being treated with risperidone" Human & Experimental Toxicology 92001) 20, 215-219, (2001).

Berke, et al. "Medical Management of Obesity", American Academy of Family Physicians, Jul. 15, 2000;62(2):419-26 ABSTRACT.

Blanchard, et al., "Pancreatitis Treated with Didanosine and Tenofabir Disoproxil Fumarate" Clinical Infectious Diseases, 2003;37 pp. 57-62.

Calabrese, et al. Letters to the Editors, "Lamotrigine and Clozapine for Bipolar Disorder" American J. of Psychiatry, vol. 157 9, Sep. 2000, 1523.

Carlsen, et al. "Evidence for dissociation of insulin-and weight-reducing effects of metformin in non-diabetic male patients with coronary heart disease" Diabetes Research and Clinical Practice Amersterdam, vol. 39, No. 1, Jan. 1998, pp. 47-54.

Carpenter, et al. "Mirtazapine Augmentation in the Treatment of Refractory Depression"; J Clin Psychiatry 60:1, Jan. 1999.

Carroll, F.I. J. Med. Chem , 46:10 (2003).

Cash, et al. "Attitudes about antidepressants: Influence of information about weight-related side effects"; Perceptual and Motor Skills, 2000, 90, 453-456.

Chen, et al. "Synergistic Effects of Cannabiniod inverse agonist AM251 and opiod antagonist namefene on food intake" Brain Res. vol. 999, Jan. 2004, pp. 22-230.

Chengappa, et al. "Changes in body Weight and Body mass index among psychiatric patients receiving lithium, valproate, or topiramate: an open-label, nonrandomized chart review" Clinical Therapeutics, 24 (10) 1576-1584 (2002).

Cone, et al. "The arcuate nucleus as a conduit for diverse signals relevant to energy homeostasis,"Int'l Journal of Obesity, 25(5):S63-S67 (2001).

Dechant et al. Drugs, 41:225-253 (1991).

Dembowski, et al. "Successful Antimanic Treatment and Mood Stabilization with Lamotrigine, Clozapine, and Valproate in a Bipolar Patient after Lithium-induced Cerebellar Deterioration" Letter Pharmacopsychiatry, 2003; 36 83-86.

Deshmukh, et al. "Managing weight gain as a side effect of antidepressant therapy"; Cleveland Clinic Journal or Medicine vol. 70, Jul. 7, 2003.

Devlin, et al. Int. J. Eating Disord. 28:325-332 (2000).

Diagnostic and Statistical Manual of Mental Disorders. 4th Edition, Text Revision, p. 583-595 (2000).

Dursen, et al., Clozapine Plus Lamotrigine in Treatment-Resistant Schizophrenia, Arch Gen Psychiatry vol. 56, Oct. 1999, 950-951.

Dursun, et al. "Lamotrgine-Clozapine Combination in Refractory Schizophrenia: Three Cases" J. Neuropsychiatry Clin. Neuroscience, 14:1, Winter 2002, 86.

Dursun, et al. "Augmenting Antipsychotic treatment with Lamotrigine or topiramate in patients with treatment-resistant Schizophrenia: a naturalistic case-series outcome study" Journal of Psychopharmacology 15(4) 2001-297-301.

Dursun, et al., "Psychopharmacology for the Clinician Psychopharmacologie Pratiqu" Journal of Psychiatry Neuroscience, vol. 26 No. 2, 2001, 168.

Dursun, et al. "Accelerated Weight Loss After Treating Refractory Depression with Fluoxetine Puls Topiramate: Possible Mechanism of Action" Canadian Journal of Psychiatry, vol. 46, No. 3 Apr. 2001, pp. 287-288.

Erez et al. J. Med. Chem., 25:847-849 (1982).

Erfuth, et al. "Bupropion as add-on strategy in difficult-to-treat bipolar depressive patients", Neurophsychobiology, vol. 45, No. Supplement 1, Mar. 2002, pp. 33-36.

Faught et al. "Randomized Controlled Trial of Zonisamide for the Treatment of Refractory Partial-Onset Seizures." Neurology; 57(10):1774-1779 (2001).

Fava, Maurizio. "Weight Gain and Antidepresants"; J Clin Psychiatry 2000;61 (suppl 11).

Fingl et al. The Pharmacological Basis of Theraputics. Ch.1, pp. 1. (1975).

Fuller et al., Fluoxetine: A Serotonergic Appetite Suppressant Drug, Drug Development Research, vol. 17, No. 1, 1989, pp. 1-15; XP009035038.

Fukagawa et al., "Monoaminergic anorectic agents", Nippon Yikurigaku Zasshi, Nov. 2001;118(5):303-8, 2001 ABSTRACT.

Gadde et al, "Zonisamide for Weight Loss in Obese Adults—A Randomized Controlled Trial", JAMA 289(14) :1820-1825 (2003).

Gadde et al, "Bupropion for Weight Loss: An Investigation of Efficacy and Tolerability in Overweight and Obese Women", Obesity Research 9(9) :544-551 (2001).
Gadde et al, "Randomized Controlled Trial of Zonisamide for Treating Obesity", American Epilepsy Society, http://164.109.45.39/submission/aes/status/..\preview.full.asp?presid=2%2E258, Sep. 11, 2002.
Gadde et al, "Randomized Trial of Weight Loss Efficacy of Zonisamide", No. 304, 26(Suppl. 1), Aug. 2002, International Journal of Obesity and Related Metabolic Disorders, Journal of the International Association for the Study of Obesity, Ninth International Congress on Obesity, Sao Paolo, Brazil, Aug. 24-29, 2002.
Gadde et al, "Zonisamide in Obesity: A 16-Week Randomized Trial", No. NR473, New Research, American Psychiatric Association 2002 Annual Meeting, May 18-23, 2002, Philadelphia, Pennsylvania.
Gadde and Logue, "Bupropion Sustained Release in Obesity: A Randomized Double-Blind, Placebo-Controlled Study", No. NR634, New Research Program & Abstracts, American Psychiatric Association, 1999 Annual Meeting, the Clinician, May 15-20, 1999, Washington, D.C.
Gadde et al. Inpharma; 1383(84):9 (2003).
Gatley, et al. European Journal of Pharmacolgy, 307:331-338 (1996).
Gehlert D.R., et al., "The Selective Norepinephrine Reuptake Inhibitor, LY368975, Reduces Food Consumption in Animal Models of Feeding", J. Pharmacology and Experimental Therapeutics Oct. 1998;287(1):122-7 ABATRACT.
Ginsberg and Sussman, "Effects of Mood Stabilizers on Weight", Primary Psychiatry 7(5):49-58 (2000).
Glass et al. Neuropeptides, 33:360-368 (1999).
Gordon, et al. "Mood Stablization and Weight Loss with Topiramate" American Journal of Psychiatry, American Psychiatric Association, Washington D.C. vol. 156, No. 6, Jun. 1999, pp. 968-969.
Grady, "Quest for Weight-Loss Drug Takes an Unusual Turn", The New York Times—Health, www.nytimes.com, Mar. 15, 2003.
Hahn, et al. J. Pharm Exper. Therapeutics 235:846-850. (1985).
Harrison's Principles of Internal Medicine. Eleventh Edition, McGraw-Hill Book Company, p. 1921-1930 (1987).
Hashiguti, et al. "Simultaneous determination of in vivo hydroxylation of tyrosine and tryptophan in rat striatum by microdialysis-HPLC: relationship between dopamine and serotonin biosynthesis"; Journal of Neural Transmission (1993) 93:213-223.
Hussey et al. J. Am. Chem. Soc., 125:3692-3693 (2003).
International Search Report PCT/US03/15703, (2003).
Islam, et al. Naltrexone, Serotonin Receptor Subtype Antagonists, and Carbohydrate Intake in Rats, Pharmacology Biochemistry and Behavior, vol. 48, No. 1, 1994, pp. 193-201; XP002292383.
Jallon et al. Drug Safety; 24(13):969-978 (2004).
Kanba et al., Progress in Neuro-Psychopharmacology and Biological Psychiatry, 18(4), 707-715 (1994).
Kanios et al, "Compositions and methods for topical administration of pharmaceutically active agents", Database USPT on WEST—USP 5,719,197, Feb. 17, 1998.
Kiptoo, et al. Enhancement of Transdermal delivery or 6-B-naltrexol via a codrug linked to hydroxyburpropion, Journal of Controlled Release 113 (2006) 137-145.
Kirkham et al. Psychopharmacology 153:267-270(2001).
Kirov, et al. Add-on topiramate reduces weight in overweight patients with affective disorders: a clinical case. BMC Psychiatry, 5:19, 8 pp. (2003).
Kolb et al. A. Pharmaceutical Res., 6:266-271 (1985).
Kossard, et al. Defining Urticarial Dermatitis; Arch Dermatol/vol. 142, Jan. 2006.
Klok et al. Macromolecules, 35:746-759 (2002).
Korner et al. "The emerging science of body weight regulation and its impact on obesity treatment," J. Clin. Invest., 111(5):565-570 (2003).
Kushner, et al. "Obesity pharmacology: past, present, and future.", Current Opinion in Gastroenterology, Mar. 2002, pp. 213-220.
Le Bourdonnec et al. J. Med. Chem., 43:2489-2492 (2000).
Leppik et al. Epilepsy Research; 14:165-173 (1993).
Lessig, et al., "Topiramate for Reversing Atypical Antipsychotic Weight Gain" J. Am. Child Adolesc. Psychiatry 40; Dec. 12, 2001. p. 1364.

Levy, et al.,"Topiramate Produced Weight Loss Following Olanzapine-Induced Weight Gain in Schizophrenia" J. Clin. Psychiatry 63; Nov. 11, 2002, 1045.
Malhotra, et al., "Medical Management of Obesity Associated With Mental Disorders", Journal or Clinical Psychiatry 2002;63[suppl 4]:24-32.
Matsuura, "Indication for Anterior Temporal Lobectomy in Patients with Temporal Lobe Epilepsy and Psychopathology", Epilepsia 41(Suppl. 9) :39-42 (2000).
McElroy et al. "Zonisamide in the Treatment of Binge-Eating Disorder: An Open-Label, Prospective Trial." J. Clin. Psychiatry; 65(1):50-56 (2004).
McElroy et al. Inpharma; 1428:10 (2004).
McLaughin, et al, Behavorial Pharmacology, 14:583:588 (2003).
Michelson, et al., "Atomexetine in the Treatment of Children and Adolescents with Attention Deficit/Hyperactivity Disorder: A Randomized, Placebo-Controlled, Dose-Response Study", Pediatrics Nov. 2001;108(5):E83 ABSTRACT.
Morris, III, "The Effect of Zonisamide Administration on Patient Weight", A Scientific Exhibit at the American Epilepsy Society Annual Meeting, Dec. 3, 2000, Los Angeles, California.
Navarro, et al. "Topiramate for Clozapine-Induced Seizures" Am. J. Psychiatry 158; 6, Jun. 2001, 968-969.
NDA20-789, ZONEGRAN (zonisamide) Capsules 100 mg, FDA Approved Labeling Text, p. 1-24 (Mar. 27, 2000).
Ninan et al. Tetrahedron., 48:6709:16 (1992).
Okada, et al. "Effects of zonisamide on extracellular levels of monoamine and its metabolite, and on Ca2+ dependent dopamine release" Epilepsy Research, 13 (1992) 113-119.
Okada, et al. "Effects of zonisamide on dopaminergic system"; Epilepsy Research 22 (1995) 193-205.
Olsen, et al., "Conjugate Addition Ligands of Opioid Antagonists. Methacrylate Esters and Ethers of 6Alpha- And 6Beta-Naltrexol", Journal of Medicinal Chemistry, American Chemical Society, vol. 33:2, 1990, 737-741.
Olszewski, et al. Evidence of Interactions Between Melanocortin and Opioid Systems in Regulation of Feeding, Neuroreort, vol. 12, No. 8, Jun. 13, 2001, pp. 1727-1730; XP009035026.
Parr et al. J. Immunol., 169:856-864 (2002).
Pasternak et al. J. of Med. Chem., 23:674-676 (1980).
Pavuluri, et al., Topiramate Plus Risperidone for Controlling Weight Gain and Symptoms in Preschool Mania, Journal of Child and Adolescent Psychopharmacology vol. 12 No. 3, 2002. p. 271-273.
Penn, et al., "Pharmacotherapy of obesity in the near term.", Current Opinion in Endocrinology and Diabetes 2003 United States, 2003, pp. 311-316.
Portoghese et al. Life Sci., 31:1283-1286 (1982).
Portoghese et al. J. Med. Chem., 29:1855-1861 (1986).
Portoghese et al. J. Med. Chem., 29:1650-1653 (1986).
Portoghese, P.S. J. Med. Chem., 35:1927 (1992).
Potter, et al. "Sustained Weight Loss Associated with 12-month topiramate Therapy" Epilepsia, Raven Press Ltd. New York, vol. 38, No. Suppl 8, 1997, p. 97.
Remington's Pharmaceutical Sciences. 18th Edition; Easton, PA: Mack Publishing Co. (1990).
Rotzinger et al., "Metabolism of some 'second' and 'fourth' generation antidepressants: iprindole, viloxazine, bupropin, mianserin, maprotiline, trazadone, nefazodone, and vanlafaxine.", Cellular and Molecular Neurobiology, 1999, 19, p. 430.
Rowland, et al. Psychopharmacology, 159:111-116(2001).
Sackellares et al. Epilepsia; 26(3):206-211 (1985).
Sashiwa et al. Macromolecules, 33:6913 (2000).
Saper et al. "The need to feed: Homeostatic and hedonic control of eating," Neuron, 36:199-211 (2002).
Sayre et al. J. Med. Chem., 27:1325 (1984).
Schmidhammer et al. A. Helv. Chim. Acta, 77:999 (1994).
Schmidt et al. Epilepsy Research; 15:67-73 (1993).
Shapiro et al. "Additive Benefits of Combination Therapy with Sibutramine and Rimonabant on Body Weight, Insulin Sensitivity and Lipoproteins in Diet-Induced Obese Mice," 2005 NAASO Annual Meeting, Poster 405-P.
Shapira et al. "Treatment of Binge-Eating Disorder with Topiramate: A Clinical Case Series." J. Clin. Psychiatry; 61(5):368-371 (2000).

Shelton, Richard C., "Classification of Antidepressants and their Clinical Implications" Primary Care Companion J. Clin. Psychiatry 2003-5 (Supp. 7) pp. 27-32.

Spigset, et al. Therapeutic Approaches to Bulimia Nervosa, Expert Opinion on Therapeutic Patents, vol. 11, No. 3, 2001, pp. 463-477; XP002292382.

Stepinski et al. Internat. J. of Peptide & Protein Res., 38:588-592 (1991).

Stromberg, et al., "A comparison of the effects of 6-beta naltrexol and naltrexone on the consumption of ehanol or sucrose using a limited-access procedure in rats." Pharmacology, Biochemistry, and Behavior, vol. 72, 483-490 (2002).

Tamiz et al. J. Am. Chem. Soc., 122:5393-5394 (2000).

Tamiz et al. J. Med. Chem., 44:1615:1622 (2001).

Thearle, et al. "Obesity and Pharmacology" Endocrinology and Metabolism Clinics of North American W.B. Suanders Company, Philadelphia US vol. 32, No. 4, pp. 1005-1024. (2003).

Tollefson, et al., Am J. Psychiatry, 154(5), 457-465 (1997).

Tutka et al, "Convulsant and anticonvulsant effects of bupropion in mice", European Journal of Pharmacology, 2004, pp. 117-120.

Vieta, et al. 1-year follow-up of patients treated with risperidone and topiramate for a manic episode. J Clin Psychiatry 64(7):834-839 (2003).

Vieta, et al. Effects on weight and outcome of long-term olanzapine-topiramate combination treatment in bipolar disorder. Journal of Clinical Psychopharmacology 24(4):374-378 (2004).

Wadden et al. "Effects of Sibutramine Plus Orlistat in Obese Women Following 1 Year of Treatment by Sibutramine Alone: A Placebo-Controlled Trial," Obesity Research; 8(6):431 (2000).

Walker et al, "Chronic Toxicity of the Anticonvulsant Zonisamide in Beagle Dogs", Fundamental and Applied Toxicology 11:333-342 (1988).

Wang, et al., "Gabapentin augmentation therapy in bipolar depression" Bipolar Disorders 2002, 4; 296-301.

Welty et al, "Weight Loss Associated With Use of Zonisamide in European and US Clinical Trials", A Compendium of Posters and Platform Sessions for Zonegran®, Presented at the Annual Meeting 2001 of the American Epilepsy Society, Nov. 30-Dec. 5, 2001, Philadelphia, Pennsylvania.

Werneke, et al. Options for Pharmacological Management of Obesity in patients Treated with Atypical Antipsychotics, International Clinical Psychopharmacology, vol. 17 No. 4, 2002, pp. 145-160; XP009035036.

Wilding. Current Drug Targets; 5:325-332 (2004).

Wilner, "Is Weight Loss With Zonisamide Gender-Specific?", Dr. Tran, 2002 Annual Meeting of the American Epilepsy Society, https://secure.neurohub.net/cgi-perl/get.cgi?pub=52318&ext=htm.

Zeng, et al. Tetrahedron Lett. 29:5123 (1988).

Zhang, et al. "Positional Cloning of the Mouse obese gen and its humane homologue" Nature 372:425-432 (1994).

Zhu, et al. Pharmacologic Treatment of Easting Disorders, Canadian Journal of Psychiatry, vol. 47 No. 3, Apr. 3, 2002 pp. 227-234; XP009035028.

Clapham et al. (2001) Anti-obesity drugs: a critical review of current therapies and future opportunities. Pharmacoloty & Therapeutics. 89:81-121.

Japanese Journal of Clinical Psychiatry (1987 16(1):123-132), and English-language version of Japanese Office Action citing the same (dated Oct. 28, 2008).

Oommen et al. (1999) Zonisamide: A new antiepileptic drug. Clinical Neuropharmacology. 22(4):192-200.

* cited by examiner

METHOD FOR TREATING OBESITY

The present application is a continuation application of and claims priority from U.S. application Ser. No. 10/830,071, filed Apr. 23, 2004, now U.S. Pat. No. 7,425,571 which is a continuation of U.S. application Ser. No. 10/440,404, filed May 19, 2003, now U.S. Pat. No. 7,109,198, which claims priority from Prov. Appln. No: 60/380,874, filed May 17, 2002, the contents of all of which are incorporated herein by reference in their entirety.

TECHNICAL FIELD

The present invention relates, in general, to obesity, and, in particular, to a method of treating obesity and minimizing metabolic risk factors associated therewith using, for example, zonisamide or other weight-loss promoting anti-convulsant either alone or in combination with bupropion or other compound that enhances the activity of norepinephrine and/or dopamine via uptake inhibition or other mechanism.

BACKGROUND

The prevalence of obesity has risen significantly in the past decade in the United States and many other developed countries, (Fiegal et al, Int. J. Obesity 22:39-47 (1998), Mokdad et al, JAMA 282:1519-1522 (1999)). Because obesity is associated with a significantly elevated risk for type 2 diabetes, coronary heart disease, hypertension, and numerous other major illnesses, and overall mortality from all causes (Must et al, JAMA 282:1523-1529 (1999), Calle et al, N. Engl. J. Med. 341:1097-1105 (1999)), weight reduction is critical for the obese patient (Blackburn, Am. J. Clin. Nujtr. 69:347-349 (1999), Galuska et al, JAMA 282:1576 (1999)). There is good evidence that pharmacotherapy can enhance weight loss when combined with interventions aimed at changing life style (National Heart, Lung and Blood Institute, Clinical guidelines on the identification, evaluation, and treatment of overweight and obesity in adults: the evidence report, NIH Publication No. 98-4083, September 1998). Yet, the available pharmacological therapies to facilitate weight loss fail to provide adequate benefit to many obese patients because of side effects, contraindications or lack of positive response (National Heart, Lung and Blood Institute, Clinical guidelines on the identification, evaluation, and treatment of overweight and obesity in adults: the evidence report, NIH Publication No. 98-4083, September 1998). Hence, there is impetus for developing new and alternative treatments for management of obesity.

Zonisamide (ZONEGRAN®) is a marketed antiepileptic drug (AED). In short-term clinical trials of zonisamide in epileptic patients taking other concomitant AEDs, a small degree of weight loss was observed as an adverse effect in a small percent of patients (Oommen and Matthews, Clin. Neuropharmacol. 22:192-200 (1999)). The anticonvulsant activity of zonisamide is believed to be related to its sodium and calcium channel (T-type) channel blocking activity (Oommen and Matthews, Clin. Neuropharmacol. 22:192-200 (1999)). This drug is also known to exert dopaminergic (Okada et al, Epilepsy Res. 22:193-205 (1995)) as well as dose-dependent biphasic serotonergic activity (Okada et al, Epilepsy Res. 34:187-197 (1999)).

Topiramate (TOPAMAX®) is an AED that has been demonstrated in clinical trials of human epilepsy to be effective as adjunctive therapy in treating simple and complex partial seizures and secondarily generalized seizures (Faught et al, Epilepsia 36(S4):33 (1995); Sachdeo et al, Epilepsia 36(S4): 33 (1995)). It is currently marketed as adjunctive therapy for partial onset seizures or primary generalized tonic-clonic seizures.

Bupropion, marketed as an antidepressant, has a pharmacological action dissimilar to that of zonisamide or topiramate. Bupropion has been shown to cause significant weight loss in patients presenting with primary obesity (Gadde et al, Obes. Res. 9(9):544 (2001)).

The present invention results, at least in part, from studies demonstrating that zonisamide is more effective than placebo for weight loss in obese subjects. The use of zonisamide (or other weight-loss promoting anticonvulsant) and bupropion (or other compound that enhances monoamine (e.g., serotonin, norepinephrine and/or dopamine) turnover in the brain via uptake inhibition or other mechanism) provides an effective treatment for obesity with few side effects.

SUMMARY OF THE INVENTION

The present invention relates generally to obesity. More specifically, the invention relates to a method of treating obesity and minimizing metabolic risk factors associated therewith using, for example, zonisamide or other weight loss-promoting anti-convulsant either alone or in combination with bupropion or other compound that enhances the activity of norepinephrine and/or dopamine via uptake inhibition or other mechanism.

Objects and advantages of the present invention will be clear from the description that follows.

DETAILED DESCRIPTION OF THE INVENTION

Figure 1:
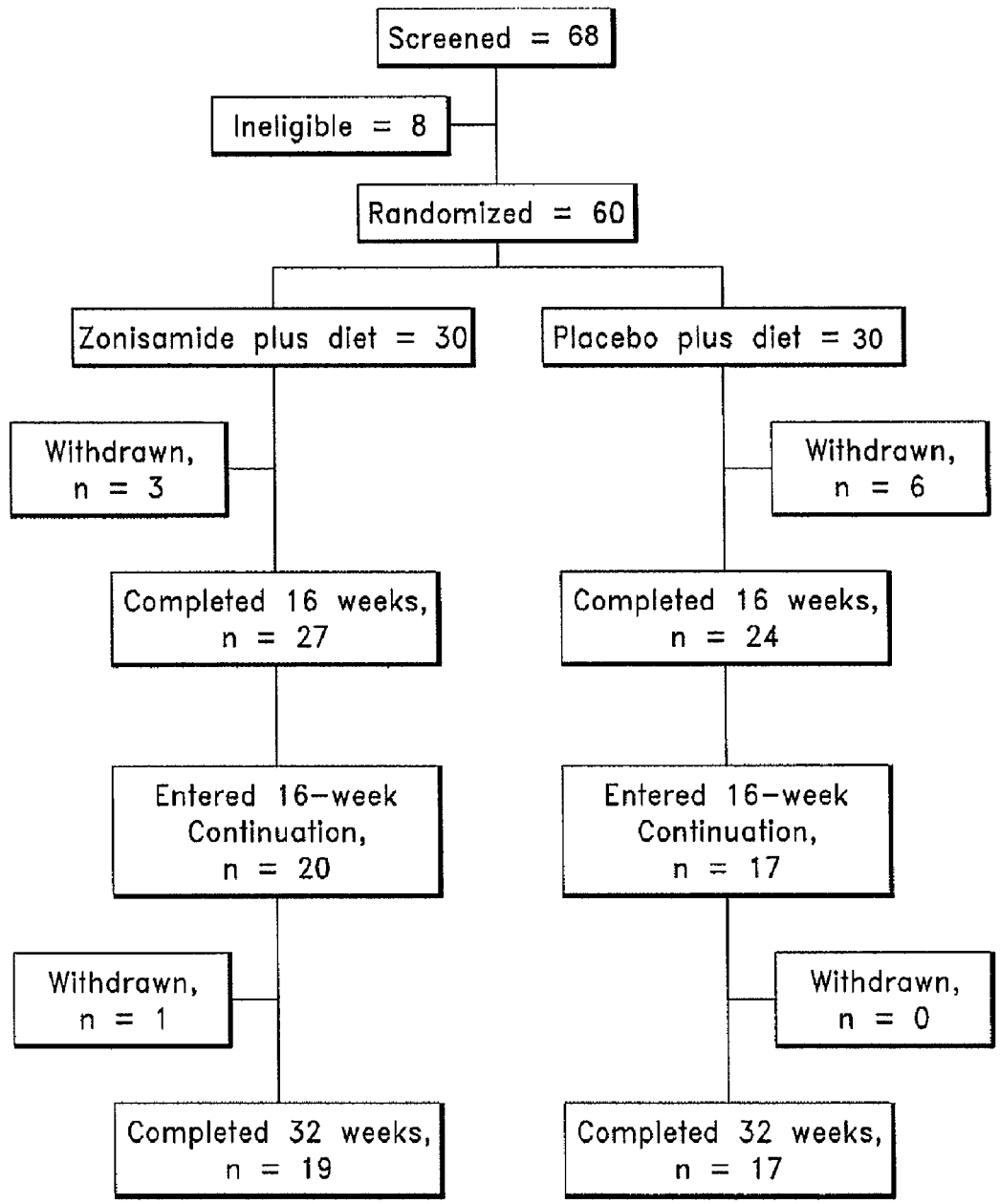
FIG. 1. Disposition of study subjects.

The present invention relates to a method of treating obesity in an animal. The invention further relates to a method of minimizing metabolic risk factors associated with obesity, such as hypertension, diabetes and dyslipidaemia. In one embodiment, the methods comprise administering to an animal in need of such treatment an effective amount of zonisamide or other weight-loss promoting anticonvulsant. In an alternative embodiment, the methods comprise administering a combination of zonisamide or topiramate, or other weight-loss promoting anticonvulsant (including agents that block kainate/AMPA (D,L-α-amino-3-hydroxy-5-methyl-isoxazole propionic acid) subtype glutamate receptors), and bupropion, or other compound that enhances the activity of norepinephrine and/or dopamine via uptake inhibition or other mechanism, in effective amounts.

Preferred active agents for use in the present invention include zonisamide or topiramate (and pharmaceutically acceptable salts thereof), however, other methane-sulfonamide derivatives, such as those described in U.S. Pat. No. 4,172,896, or other sulfamates (including sulfamate-substituted monosaccharides), such as those described in U.S. Pat. No. 4,513,006, can also be used. While the use of bupropion is also preferred, compounds disclosed in U.S. Pat. Nos. 3,819,706 and 3,885,046 can be used, as can other compounds that enhance the activity of norepinephrine and/or dopamine via uptake inhibition or other mechanism (e.g., Atomoxetine or Reboxetine).

As used herein, the term "obesity" includes both excess body weight and excess adipose tissue mass in an animal. An obese individual is one (e.g., 21-50 years old) having a body mass index of $\geq 30$ kg/m$^2$. While the animal is typically a human, the invention encompasses the treatment of non-human mammals.

The amount of active agent(s) (e.g., zonisamide alone or in combination with, for example, bupropion) administered can vary with the patient, the route of administration and the result sought. Optimum dosing regimens for particular patients can be readily determined by one skilled in the art.

When zonisamide is used alone, the dose can be from about 25 mg to about 800 mg per day, generally given once per day or divided (e.g., equally) into multiple doses. Preferably, the dose is from about 100 mg to about 600 mg per day, more preferably, the dose is from about 200 mg to about 400 mg per day. However, it may be necessary to use dosages outside these ranges.

When the combination therapy is used, the daily dose of, for example, zonisamide can be from about 25 mg to about 800 mg, preferably from about 100 mg to about 600 mg, more preferably from about 200 mg to about 400 mg. When topiramate is used in combination therapy, the daily dose of topiramate can be from about 25 mg to about 1600 mg, preferably from about 50 mg to about 600 mg, more preferably from about 100 mg to about 400 mg. The daily dose of bupropion used can be from about 25 mg to about 600 mg, preferably from about 50 mg or about 150 mg to about 450 mg. The doses can be given once per day or divided (e.g., equally) into multiple doses. It may be necessary to use dosages outside these ranges. When the combination therapy is used, the ratio of zonisamide (or topiramate) to bupropion can range, for example, from about 2:1 to about 1:2.

When the combination therapy is used, the individual components of the combination can be administered separately at different times during the course of therapy or concurrently in divided or single combination forms.

In accordance with the present invention, the active agent(s) (e.g., zonisamide alone or in combination with bupropion) can be administered in any convenient manner, such as orally, sublingually, rectally, parentally (including subcutaneously, intrathecarly, intramuscularly and intravenously), or transdermally. The most preferred route of administration is the oral route.

The active agents of the invention can be administered in the form of a pharmaceutical composition or compositions that contain one or both in an admixture with a pharmaceutical carrier. The pharmaceutical composition can be in dosage unit form such as tablet, capsule, sprinkle capsule, granule, powder, syrup, suppository, injection or the like. Sustained released formulations can also be used. The composition can also be present in a transdermal delivery system, e.g., a skin patch.

Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

In accordance with the invention, the combination of, for example, zonisamide or topiramate and bupropion (including sustained release preparations) is an effective treatment for obesity and provides an effective means of minimizing metabolic risks associated with obesity. The combination can be more effective than, for example, zonisamide or topiramate treatment alone and with fewer side effects. Neuropharmacologically, all three major nerve transmitters that regulate appetite and weight, i.e., seratonin, norepinephrine and dopamine, are targeted with the combination of, for example, bupropion and zonisamide or topiramate. Side effects of, for example, zonisamide or topiramate (such as somnolence, psychomotor slowing, cognitive impairment, fatigue and depression) can be offset by insomnia, activation, psychomotor agitation and antidepressant effects of, for example, bupropion. On the other hand, zonisamide or topiramate, for example, can reduce the seizure risk associated with, for example, bupropion. Lower doses of both types of medication can be used in the combination treatment, thereby further reducing the overall side effect burden.

Certain aspects of the invention are described in greater detail in the non-limiting Examples that follow and in Gadde et al, JAMA 289:1820 (2003). (See also U.S. Pat. Nos. 6,323,236, 6,071,537, 6,548,551, 6,506,799 and 6,191,117.)

EXAMPLE 1

Experimental Details

Subjects

Sixty-eight subjects were screened for participation and 60 subjects were randomized.

Inclusion criteria were: male or female, aged 21-50 years, with body mass index (BMI) of $\geq 30$ kg/m$^2$.

Exclusion criteria were: obesity of a known endocrine origin, such as hypothyroidism and Cushing's syndrome; serious/unstable medical or psychiatric illness; current major psychiatric disorder; current drug or alcohol abuse; history of or current kidney disease or renal calculi; significant liver disease; uncontrolled hypertension; current diabetes mellitus (DM), type 1 or 2 DM receiving pharmacotherapy; untreated or uncontrolled thyroid disease; weight loss or gain greater than four kilograms in past three months; history of obesity surgery; current or recent use of any weight loss medications, herbs, or supplements; current or recent use of drugs, herbs, or dietary supplements known to significantly affect body weight; concomitant medications that significantly affect P450 3A4 hepatic microsomal enzymes; hypersensitivity to sulfonamides; women of child-bearing age not adhering to an acceptable form of contraception; pregnant or breast-feeding women; and, subjects judged to be unable to follow instructions and study procedures.

Study Design

The study had two phases. The first was the acute phase—a 16-week, randomized, double blind, parallel-group comparison of zonisamide (ZON) and placebo (PBO). This was followed by an optional 16-week extension phase. At the end of the acute phase, subjects wishing to continue further received the same treatment for an additional 16 weeks in a single-blinded fashion.

Randomization, Medication Dosing and Dispensing

The subjects were randomized in a 1:1 ratio to receive zonisamide or placebo capsules. Study medication was dispensed under blinded conditions through computer-based randomization. The randomization was generated using a random number table with a block size of ten. There was no stratification by gender or other demographics. The study investigators were blind to the "blocking" method used by the pharmacy. The treatment assignment codes were not available to the investigators until all subjects completed the acute phase, the data were entered, and the database for this phase was locked, meaning that no further changes could be made to the data.

The study medication was dispensed in the form of capsules. Each capsule contained either 100 milligrams zonisamide or placebo. The capsules were made to look identical. The dose escalation was as follows: one capsule (zonisamide 100 mg or placebo) every evening for the first 2 weeks; two capsules (zonisamide 200 mg or placebo) every evening during Weeks 3 and 4; three capsules (zonisamide 300 mg or placebo) every evening during Weeks 5 and 6; and, four capsules (zonisamide 400 mg or placebo) every evening from Week 7 onward. At Week 12, the dose could be increased further to six capsules (zonisamide 600 mg or placebo) every evening for subjects who had not lost at least 5% of their initial body weight. If a subject preferred not to take all six capsules at one time, taking a half of the daily dose in the morning was an option. Based on tolerability, dose escalation could be withheld, or the dose might also be decreased. Medication compliance was overseen by recording the number of tablets returned and comparing this number to the number of capsules dispensed at each visit.

Diet and Lifestyle Counseling

Subjects in both treatment groups were instructed to follow an individual diet that was 500 Kcal/day less than what they needed to maintain their weight. The prescribed diet, based on eating a variety of foods from the Food Guide Pyramid, emphasized decreasing portions, eating more fruits and vegetables, and drinking 8 cups of water each day. Increased physical activity was also encouraged for subjects in both groups. Subjects were asked to record their dietary intake including portion sizes in food diaries, which were provided to them. A registered dietician reviewed food diaries and provided counseling to all subjects. Subjects were encouraged to make healthy changes in their diets and physical activity that could be maintained after the completion of the study.

Visits and Measurements

Subjects were seen at weeks 0, 2, 4, 8, 12, and 16 in the acute phase, and every four weeks in the extension phase. During each visit, the following assessments were performed: blood pressure, heart rate, weight, dietary compliance, medication accountability and tolerability, and adverse effects. Body weight was measured on a calibrated electronic scale to the nearest 0.1 kilogram. A registered dietitian reviewed food diaries and assessed dietary compliance. Adverse effects were gathered via spontaneous reporting by subjects as well as open-ended inquiries by the clinicians. Reportable adverse effects were new symptoms or illnesses that emerged during treatment or those that had an increase in severity compared with baseline.

In addition to the above, the subjects completed the Impact of Weight on Quality of Life (IWQOL) (Kolotin et al, Obesity Res. 3:49-56 (1995)) at baseline, Week 8, and Week 16. The IWQOL is a self-report measure with 74 items that assess the perceived effect of weight on quality of life in the following domains (subscales)—health, social/interpersonal life, work, mobility, self-esteem, sexual life, activities of daily living, and eating (comfort with food). Improvement with treatment is reflected by decreasing scores on all the subscales with the exception of the eating (comfort with food) subscale, which is expected to show less comfort around food with effective treatment. Body composition (fat and lean masses) and bone mineral density (BMD) were determined, at baseline and Week 32, by dual x-ray absorptiometry (DXA; Hologic 2000, Waltham, Mass.). All DXA measurements were gathered using the same equipment and techniques. Subjects were instructed to fast for 8 hours and not to drink water or other beverages for at least 4 hours prior to DXA measurement.

Endpoints and Measures of Outcome

Body weight was the primary end point. Examined were the absolute change in weight, percent change in weight, and the number of subjects in each group that achieved weight losses of 5% and 10%. Secondary outcome measures included heart rate, blood pressure, frequency of adverse effects, fasting electrolytes and lipids, waist measurement, VAS-C, IWQOL, body composition and BMD.

Statistical Analysis

All randomized subjects were included in the primary analysis. Putative differences between subjects in the zonisamide group versus subjects in the placebo arm were tested using Student's t-test for continuous variables and Fisher's exact test for categorical covariates. A dichotomous proxy variable denoting attrition status was also tested between groups using Fisher's exact test. Two subjects that withdrew after completing only the baseline interview were excluded from subsequent analyses.

Weight change during the study was assessed in terms of actual weight change over the six study intervals using multivariable regression methodology, and as a dichotomous outcome of 'response,' i.e., 5% weight loss at Week 16, and 5% and 10% weight loss at Week 32. The proxy variables denoting response status were tested across treatment conditions again using Fisher's exact test. Three multivariable regression analyses were conducted. In the first, body weight at each time point was modeled using a random effects growth curve model. Heuristically, the model fits a regression line for each subject using available data points, thus maximizing use of actual data. For the second set of analyses, body weights were regressed as above with missing observations carried forward from the last recorded weight based on an intent-to-treat approach (LOCF). The final model was restricted to the subset of respondents with no missing data (completers). All models included covariates for gender and BMI as well as proxy variables denoting treatment condition, time, and a term for the interaction of treatment with time; age race, and percent body fat at baseline were not significantly associated with weight loss and, hence, excluded from the above models.

Secondary analyses were conducted over three general areas of interest. In each case, analyses were based on 2×2 repeated measures ANOVAs that included time, drug condition, and their interaction (time-by-drug). The primary interest in each instance was to determine if subjects in the zonisamide condition were differentially affected relative to controls as operationally determined by testing the significance of the estimated interaction term. Tests in first area of interest focused on clinical indicators including levels of creatinine, glucose, triglycerides, high and low density lipoproteins (all assessed at baseline and study conclusion), waist measurements (baseline, Week 8 and Week 16), blood pressure (systolic and diastolic), and heart rate. The second general area of sampled quality of life indicators including activities of daily living, appetite, esteem, health, interpersonal relations, mobility, sex, and work using the IWQOL Scale; repeated measurements were taken at baseline, Week 8, and Week 16). The final set of secondary analyses sampled hunger and appetite using the Visual Analogue Scale for Hunger and Food Cravings. Categories sampled included sweets, breads, salts, fats, meats, sodas, and overall hunger. Measurements were sampled at baseline, Week 8, and Week 16.

The frequency of occurrence of individual adverse effect was tested across drug conditions using Fisher's exact test.

Results

Subject Characteristics and Disposition

Of the 68 subjects screened for participation, 8 were ineligible (FIG. 1). Sixty subjects were randomized—30 to receive zonisamide (ZON) and 30 placebo (PBO). Nine subjects—6 in the PBO group and 3 in the ZON group—dropped out of the acute phase; thus, 51 of 60 subjects completed the first 16 weeks. The attributed reasons for premature discontinuation were: adverse events (ZON 1, PBO 2), lost to follow-up (ZON 1, PBO 2), consent withdrawn (ZON 0, PBO 2), and protocol violation (ZON 1, PBO 0).

With regard to characteristics of subjects at baseline (Table 1), there were no significant differences between the treatment groups with the following exceptions: with regard to gender distribution, there was a marginal difference (p=0.08) as all five men in the study were randomized to ZON. Baseline BMI was slighter lower (p=0.07) in the ZON group.

TABLE 1

Baseline Characteristics of the Subjects

| Characteristic | Zonisamide (n = 30) | Placebo (n = 30) |
|---|---|---|
| Age, yrs | 37.5 (1.3) | 36.4 (1.6) |
| Sex, No. | | |
| Men | 5 | 0 |
| Women | 25 | 30 |
| Race, No. | | |
| Black | 12 | 17 |
| White | 18 | 13 |
| Weight, kg | 98.2 (2.5) | 97.8 (2.6) |
| BMI, kg/m$^2$ | 35.4 (0.7) | 37.2 (0.8) |
| Body fat, % | 40.8 (0.9) | 42.6 (0.8) |

Age, weight, BMI and body fat are presented as group means (SE).
BMI denotes body mass index, defined as weight in kilograms divided by the square of height in meters.

Presented first are the results of the acute phase (initial 16-week treatment), which was double-blind, and included all randomized subjects. Since the extension phase was optional and single-blind, all the important results from this phase are presented separately.

Dose

The prescribed mean highest daily dose of zonisamide was 427 (29) mg, corresponding to 4.27 capsules, whereas the placebo group received 5.00 capsules (corresponding to 500 mg).

Weight Loss

Percent and Absolute Change in Weight

Figure 2:
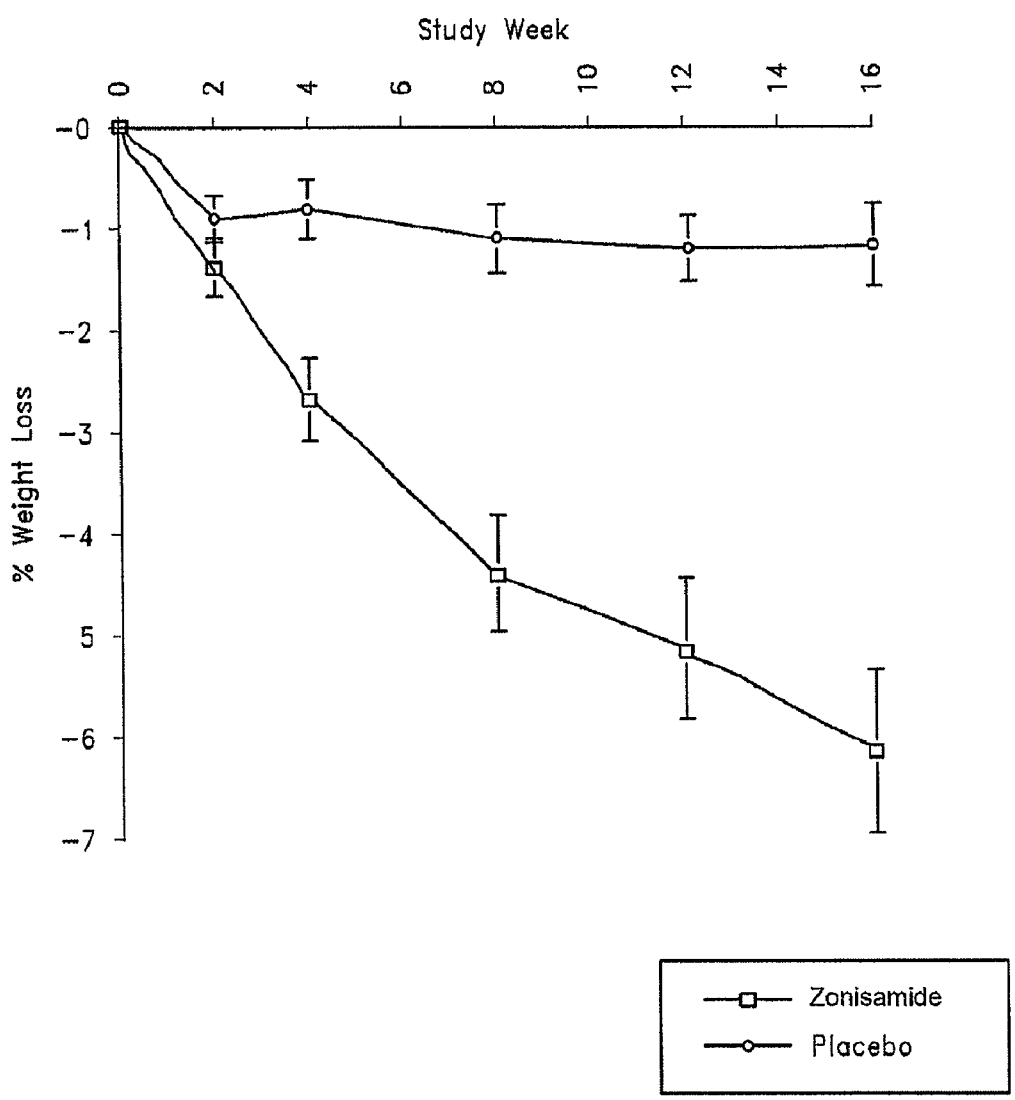
FIG. 2. Pattern of weight change from baseline to Week 16 in obese subjects who received zonisamide (n=30) or placebo (n=30). Results plotted as means (SE). Data are from the last observation-carried-forward (LOCF) analysis.

The curves for weight change as a percent weight loss over the 16-week duration for zonisamide and placebo groups are shown in FIG. 2 for subjects in the intent-to-treat (ITT) analysis with LOCF. The mean (SE) estimated weight loss for the zonisamide group (n=30) was 5.98% (0.82%) compared with 1.02% (0.40%) for the placebo group (n=30); time×treatment interaction was significant ($F_{1,58}$=22.05; p<0.0001) For the ITT-LOCF population, the absolute weight changed for the zonisamide group from 98.17 (2.5) kg at baseline to 92.28 (2.47) kg at Week 16 whereas for the placebo group, the corresponding change was 97.75 (2.63) kg to 96.86 (2.78) kg (time×treatment: $F_{1,58}$=24.65; p<0.0001). Results from random coefficient regression analyses supported differential weight loss for zonisamide-treated subjects. Regardless of imputation procedure, the drug-by-time interaction differed significantly from zero in all models. For the likelihood imputed model, the estimated regression coefficient associated with the interaction term predicted weight loss per week in excess of 0.3 kg over the course of the study; complimentary values for the other two models were 0.29 kg/wk using LOCF intent-to-treat imputation, and 0.21 kg/wk as estimated from the model based only on complete-data subjects. Among the remaining covariates, female gender was associated with significantly lower weight levels, while higher BMI scores were associated with increasing weight levels, again irrespective of model.

For the subset of subjects completing the 16-week acute phase, the difference between treatment groups in the achieved weight loss over time was again significant ($F_{1,49}$=20.07; p<0.0001) with the ZON group losing 6.61% (0.81%) weight compared with the placebo group losing 1.30% (0.49%).

Responders (≧5% and ≧10% Weight Loss)

In the ITT-LOCF population, 17 of 30 subjects (57%) in the ZON group and 3 of 30 subjects (10%) in the PBO group achieved weight loss of ≧5% weight loss at Week 16 (Fisher's Exact; p<0.0003); 7/30 ZON subjects and 0/30 PBO subjects achieved ≧10% weight loss at Week 16 (p<0.0053).

Other Efficacy Measures

Waist circumference decreased more in the zonisamide group over the 16 weeks (103.5 [1.6] cm to 97.2 [1.8] cm vs. 103.2 [1.9] cm to 100.5 [2.0] cm; time×treatment: $F_{1,49}$=7.75; p<0.0008). Heart rate decreased by an average of approximately 2 beats/min in the overall sample (p<0.0007) although there was no difference between the groups. Systolic and diastolic blood pressure readings did not change by four months.

Safety Measures

Subjects assigned to ZON reported, on average, 2.1 adverse effects (AEs) over the study period compared with 1.6 AEs for PBO (t=−1.56; p<0.125). Of the individual AEs, 10 subjects in the ZON group and 1 in the PBO group reported fatigue (Fisher's Exact; p<0.006); there were no other AEs that were reported differently by the treatment groups. Serum creatinine increased from 0.79 (0.03) mg/dL at baseline to 0.92 (0.03) mg/dL with zonisamide treatment while the change for PBO was 0.76 (0.02) mg/dL to 0.79 (0.02) mg/dL ($F_{1,49}$=14.82; p<0.0003).

Extension Phase Results

Of the 37 subjects (ZON 20, PBO 17) who entered the extension phase, 36 completed Week 32. One subject in the ZON group withdrew prematurely citing time constraints. Ten of 19 zonisamide subjects and none of the placebo subjects lost ≧10% weight at Week 32 (p<0.0004). Zonisamide subjects had a mean weight loss of 9.37% (1.64%) at Week 32 compared with 1.82% (0.73% for placebo subjects ($F_{1,34}$=13.02; p<00001). With regard to absolute weight in kilograms, the change over the 32 weeks for the ZON group was from 96.88 (3.01) kg to 87.64 (2.95) kg contrasting with change in the placebo group from 96.39 (2.95) kg to 94.85 (3.38) kg (time×treatment: $F_{1,34}$=14.76; p<0.0001).

Waist circumference decreased more in the zonisamide group over the 32 weeks (103.5 [2.0] cm to 93.6 [2.2] cm vs. 103.8 [2.4] cm to 100.5 [2.5] cm; time×treatment: $F_{1,34}$=8.38; p<0.0001). Both treatments led to decrease in systolic blood pressure; however, the decrease was greater in the ZON group (129.1 [2.5] mmHg to 122.3 [1.8] mmHg vs. 128.2 [1.8] mmHg to 126.8 [1.8] mmHg; time×treatment: $F_{1,34}$=2.72; p<0.0047). Diastolic blood pressure decreased with ZON treatment, but not with PBO (82.5 [1.8] mmHg to 79.7 [1.2] mmHg vs. 82.5 [1.8] mmHg to 82.2 [1.1] mmHg; time× treatment: $F_{1,34}=1.99$; $p<0.0403$). Heart rate showed no significant change with either treatment.

Bone mineral density at lumbar vertebrae (L-BMD) did not change over time in either group. Total bone mineral density showed a small, but statistically significant ($p<0.017$) increase in both groups although not clinically significant; there was no difference between the groups in this regard.

The following measures of the Impact of Weight on Quality of Life (IWQOL) scale improved more significantly in the zonisamide group over the placebo group at Week 32: Health ($p<0.0030$), Work ($p<0.0651$), Mobility ($p<0.0019$), and Activities of Daily Living ($P<0.0005$).

Serum creatinine increased from 0.78 (0.03) mg/dL at baseline to 0.92 (0.03) mg/dL with zonisamide treatment while the change for PBO was 0.75 (0.02) mg/dL to 0.77 (0.02) mg/dL ($F_{1,34}=11-01$; $p<0-0001$). No clinically significant changes in mean lipid values were observed with either treatment although significant reductions were observed for some subjects.

CONCLUSION

This randomized study demonstrated that zonisamide produced a robust weight loss effect when used as an adjunct to a standard, but low-key dietary and lifestyle intervention. The drug's superior effect over placebo was demonstrated in the various analyses conducted for both the acute phase (first 16 weeks) as well as the extension phase. The difference in the weight loss efficacy between the active treatment and placebo was evident by 4 weeks and the gap widened as the study progressed. Given the low-key adjunctive dietary and lifestyle intervention provided in this study, weight loss of 9.4% at 32 weeks can be regarded a significant finding.

Reductions in certain risk factors associated with obesity were also observed. Waist circumference decreased more significantly with zonisamide therapy compared with placebo treatment, likely related to greater degree of weight loss with active treatment. There was also a meaningful reduction in systolic blood pressure although the subjects were not hypertensive at study entry. Improvements were also noted in mobility, general health, occupational functioning, activities of daily living, reflecting an overall improved quality of life. No significant changes in mean lipid levels were observed although significant reductions were seen for some subjects.

Zonisamide was generally well tolerated. Fatigue was the only adverse effect that occurred at a higher frequency than with placebo treatment. Although not observed frequently in this study, the following adverse effects occurred frequently in the zonisamide epilepsy trials: dizziness, cognitive impairment, and somnolence. Zonisamide is a sulfonamide; there is a potential for hypersensitivity reactions. Serious hematologic events have also been reported. The risk of kidney stones also needs recognition. For the duration of treatment in this study (approximately 8 months), the rate of occurrence of kidney stones with zonisamide therapy is estimated to be 62.5 per 1000 patient-years of exposure. Consistent with data from epilepsy trials, an increase in serum creatinine was noted with zonisamide therapy, but not with placebo. Whereas the increase (approximately 16% increase) was significant, there was no further increase in the extension phase; no value exceeded the upper limit of normal range and there were no clinical events associated with the increase.

EXAMPLE 2

A 35 y.o. obese female (weight 271 lb, BMI 40 kg/m$^2$) who failed to benefit from numerous weight loss interventions, was started on bupropion 150 mg/day and the dose was increased after 5 days to 150 mg twice a day. After one month of treatment, she lost 5 lbs, but regained 3.4 lbs during the second month—thus managing a net weight loss of 1.6 lbs after 2 months on bupropion. At this point, zonisamide was added to the regimen at 100 mg/day and the dose was increased after 2 weeks to 200 mg/day. After one month on the combination therapy, the patient had lost 11 lbs and reported no side effects. No further information is available as the patient has relocated.

EXAMPLE 3

A 47 y.o. obese female (weight 246 lb, BMI 41.4 kg/m$^2$) who had not benefited from various treatments, was started on zonisamide 100 mg/day and the dose was increased gradually to 400 mg a day over the next 4 weeks. After one month of treatment, she lost 4.6 lbs, but there was no further weight loss during the second month. At this point, zonisamide dose was increased to 600 mg a day; the patient achieved an additional weight loss of 0.6 lb in the next month. Thus, after 3 months of zonisamide therapy, the total weight loss with zonisamide therapy was 5.2 lb. Zonisamide was continued at the same dose and bupropion SR was started at 100 mg a day. After 10 days, the dose of bupropion was increased to 200 mg a day. One month later, the patient had lost 8.2 lbs and reported no side effects. She reported that she felt "full" after eating small portions of food, and had more energy. She had lost over 35 lbs over ten months on the combination therapy with no side effects.

EXAMPLE 4

A 46 y.o. obese female received zonisamide in a clinical trial and achieved weight loss of 35.6 lb over 32 weeks. During the 5 weeks following discontinuation of zonisamide, she gained 7.7 lb. Zonisamide was restarted, but this intervention was unsuccessful in offsetting the regained weight; after 16 weeks of therapy at doses up to 400 mg/d, the patient gained 1.2 lb. At this point, bupropion was added at 150 mg/d. After 14 weeks of combined therapy, the patient lost 9.4 lb with no adverse effects.

All documents cited above are hereby incorporated in their entirety by reference.

What is claimed is:

1. A method of reducing the weight of an overweight subject, said method comprising: identifying an overweight subject and administering to said overweight subject a pharmaceutical composition comprising a sustained release formulation of zonisamide, or a pharmaceutically acceptable salt thereof, in an amount effective to reduce the weight of said subject.

2. The method according to claim 1, wherein said effective amount of zonisamide is in the range of about 25 to about 800 mg/day.

3. The method according to claim 2, wherein said effective amount of zonisamide is in the range of about 100 to about 600 mg/day.

4. The method according to claim 1, wherein said overweight subject is an obese subject.

5. The method according to claim 1, wherein said pharmaceutical composition is administered in combination with a reduced calorie diet or increased physical activity.

6. A method of reducing weight in an overweight subject, said method comprising: identifying an overweight subject and administering to said overweight subject a pharmaceutical composition comprising a sustained release formulation of zonisamide, or a pharmaceutically acceptable salt thereof, in an amount effective to induce weight loss in said subject, wherein the weight loss is ≧5%, or wherein said weight loss continues during the period of administration of said pharmaceutical composition.

7. The method according to claim 6, wherein said effective amount of zonisamide is in the range of about 25 to about 800 mg/day.

8. The method according to claim 6, wherein said effective amount of zonisamide is in the range of about 100 to about 600 mg/day.

9. The method according to claim 6, wherein said overweight subject is an obese subject.

10. The method according to claim 6, wherein said pharmaceutical composition is administered in combination with a reduced calorie diet or increased physical activity.

11. A method of treating obesity by reducing the weight of an obese subject, said method comprising: identifying an obese subject and administering to said obese subject an effective amount of a pharmaceutical composition comprising a sustained release formulation of zonisamide, or a pharmaceutically acceptable salt thereof.

12. The method according to claim 11, wherein said obese subject has a BMI of at least 30 $kg/m^2$.

* * * * *